(12) United States Patent
Lezdey et al.

(10) Patent No.: US 6,537,968 B1
(45) Date of Patent: *Mar. 25, 2003

(54) TREATMENT OF LUPUS ERYTHEMATOSUS

(75) Inventors: Darren Lezdey, Indian Rocks Beach, FL (US); Jarett Lezdey, Indian Rocks Beach, FL (US)

(73) Assignee: Alphamed Pharmaceuticals Corp, Clearwater, FL (US)

( * ) Notice: Subject to any disclaimer, the term of this patent is extended or adjusted under 35 U.S.C. 154(b) by 33 days.

This patent is subject to a terminal disclaimer.

(21) Appl. No.: 09/624,442

(22) Filed: Jul. 24, 2000

(51) Int. Cl.[7] .................. A61K 38/00; A61K 38/16; C07K 14/00
(52) U.S. Cl. ............... 514/12; 514/2; 514/21; 514/559; 514/706; 514/707; 514/851; 514/861; 514/863; 514/912; 530/328; 530/350; 424/493; 424/491; 435/183; 435/219
(58) Field of Search ................. 514/2, 12, 21, 514/559, 706, 707, 851, 861, 863, 912; 530/350, 328; 424/493, 491; 435/183, 219

(56) References Cited

U.S. PATENT DOCUMENTS 5,503,852 A * 4/1996 Steiner et al. ............ 424/493
5,620,708 A * 4/1997 Amkraut et al. .......... 424/491

OTHER PUBLICATIONS

Lacki et al., Lupus, vol. 4, pp. 221–224, 1995.*

* cited by examiner

Primary Examiner—Christopher S. F. Low
Assistant Examiner—Chih-Min Kam
(74) Attorney, Agent, or Firm—John Lezdey

(57) ABSTRACT

The present invention provides for the treatment of an individual suffering from lupus erythematosus utilizing a serine protease inhibitor. The treatment includes the use of a corticosteroid that is administered separately or in combination. The serine proteases preferred are alpha 1-antitrypsin, secretory leucocyte protease inhibitor, alpha 2-macroglobulin or mixtures thereof.

12 Claims, No Drawings

TREATMENT OF LUPUS ERYTHEMATOSUS

FIELD OF THE INVENTION

The present invention relates to the treatment of lupus erythematosus. More specifically, there is provided the treatment of inflammatory conditions, rashes or lesions which occur with patients with systemic lupus erythematosus (SLE) by the administration of protease inhibitors.

BACKGROUND OF THE INVENTION

The common treatment for lupus erythematosus involves the H use of several drugs as well as sunscreens. Hydroxychloroquine alone or in combinations with oral steroids is used. Topical steroids and/or vitamin A are also used for treating skin eruptions. The patients with severe SLE involving several organs have been treated with immunosuppressive agents (corticosteroids and pulse cyclophosphamide therapy). The treatments have not been effective in many cases and have resulted in other problems resulting from an overuse of steroids.

In many cases, the presence of the skin lesions results in keloid scarring. The use of steroids not only does not prevent the scarring but can lead to thinning of the skin so as to lead to further lesions.

Systemic lupus erythematosus, is a chronic rheumatic disease in which connective tissue throughout the body becomes inflamed. It is an autoimmune disorder in which inflammation is caused by antibodies that attack normal body tissue as if it were an outside invader. The precise cause is unknown, but researchers believe that certain people inherit a genetic predisposition to the disorder, which is then triggered by a virus or some other unidentified environmental factor.

The disease strikes women about 10 times as often as men. It can develop at any age, but is most common in young adults. Symptoms range from so mild that SLE goes undetected for long periods to disabling, even life threatening.

Lupus is often described as the great pretender among Ad diseases because it causes such a wide range of symptoms, the most common of which are fatigue and joint pain. But other manifestations may include a chronic low-grade fever, hair loss, dry eyes and mouth, muscle aches, swollen lymph nodes, loss of appetite, nausea, and mouth ulcers.

About half of all patients develop a butterfly-shaped rash over the nose and cheeks. Depending upon the organs affected, SLE may also cause severe headaches, anemia, inflammation in the lining of the heart or lungs, kidney failure, and mental disorders.

A variation—discoid lupus erythematosus—affects mainly the skin. A rash may appear not only on the face but also on the neck, scalp, and other areas. It ranges from a mild scaliness to a widespread blistery eruption.

As in many other rheumatic disorders, symptoms come and go unpredictably. Sun exposure or stress often produces a flare-up. During pregnancy, symptoms can worsen and cause miscarriage.

It has now been found that mast cells play a role in the formation of the lesions and inflammation. The presence of cathepsin G and elastase in excess results in the poor laying down of tissue so as to result in scarring. The swollen joints result from an inflammatory condition.

Alpha 1-antitrypsin (AT) belongs to the serpin superfamily of serine protease inhibitors. It is a small glycoprotein which is mostly synthesized in the liver and has a molecular weight of 53,000 daltons. Human proteinase inhibitors are involved in the regulation of proteolysis, such as the coagulation pathway, fibrinolysis, tissue destruction by endogenous serine proteinases and inflammation.

U.S. Pat. No. 5,492,889 to Lezdey et al, which is herein incorporated by reference, disclosed the treatment of mast cell tumors by the administration of alpha 1-antitrypsin alone or in combination with other serine protease inhibitors.

SUMMARY OF THE INVENTION

The present invention provides a method of treating lupus erythematosus and more particularly to skin eruptions and inflammations resulting from the disease.

According to one embodiment of the invention, there is provided the treatment of symptoms of lupus erythematosus, and in particular, the administration of a serine protease inhibitor. More specifically, according to one embodiment, the treatment provides topically applying a composition containing an effective amount of a serine protease inhibitor selected from the group consisting of alpha 1-antitrypsin, secretory leucocyte protease inhibitor (SLPI), alpha 2-macroglobulin and mixtures thereof to the site of the disease.

Advantageously, the composition includes an effective amount of arginine or an arginine containing amino acid to help in penetration of the drug into the skin.

According to another embodiment of the invention there is provided the treatment of individuals having a lupus disease associated with skin eruptions by treatment with protease inhibitors which prevent the degranulation of mast cells, controls the levels of tryptase, prevent or control the release of histamine and prevent scarring. The treatment includes providing a composition for topical administration. Preferably, a combination therapy is used to treat both the disease and the symptoms.

It is a general object of the invention to provide a composition and method for treating lupus erythematosus.

It is a further object of the invention to prevent scarring by individuals with SLE.

It is yet another embodiment to treat the inflammation which results in patients with SLE.

DESCRIPTION OF THE PREFERRED EMBODIMENTS

In accordance with one embodiment of the invention, there is provided a method for the treatment of individuals suffering from lupus erythematosus or symptoms thereof by the administration of a serine protease inhibitor. The method consists of the administration of an effective therapeutic amount of a protease inhibitor selected from the group consisting of alpha 1-antitrypsin, secretory leucocyte, protease inhibitor, alpha 2-macroglobulin or mixtures thereof, and analogs or derivatives thereof in a suitable pharmaceutical carrier.

Accordingly, a composition containing about 0.5 to 10 mg. of protease inhibitor is in a suitable pharmaceutical vehicle is used in the treatment. Generally, for topical use, about 1 to 5 mg. of the protease inhibitor has been effective to treat the eruption and to prevent scarring.

Preferably, about 1 to 5 mg of the protease inhibitor in its natural, transgenic or recombinant form is placed into a composition for topical application such as a cream, gel, ointment or the like. A corticosteroid may be included in the treating composition. The treatment provides immediate relief of pain since the kinins and kallikreins can be controlled. The patient can be treated daily until the lesions are reduced and under normal bodily control. In severe cases, oral corticosteroids may be utilized. The composition may also include penetrating agents such as hyaluronic acid, insulin, liposome, or the like, as well as L-arginine or the arginine containing amino acids. The penetrants may be used in an amount of about 0.5 to 2% by weight of composition. Hyaluronic acid also aids in wound healing.

Systemic lupus erythematosus may also be treated by weekly infusion of 200 mg of the serine protease inhibitor in a 2% saline solution or by oral dosages daily of the inhibitor in a carrier which transgresses the gastric barrier.

It has been found that the incorporation of L-arginine or an arginine containing amino acid having up to ten carbon atoms helps in the penetration of the drug into the skin. The arginine also attracts hormones to the site to help in wound healing.

Serine protease inhibitors have been found to play a major role in the direct inactivation of the mediators of inflammation. The almost immediate disappearance of pain indicates that there can be a control of the kinins as well. A cocktail of serine protease inhibitors, their analogs, salts or derivatives, appears to provide the quickest healing when used in combination with a corticosteroid.

The drug can be administered topically in unit dosage form containing about 1 to 5 mg per day depending on the severity of the disease. The use of controlled release substances, for example, liposomes, diketopyperazine microparticles as disclosed by U.S. Pat. Nos. 5,620,708 and 5,503,852 which are herein incorporated by reference, or an occlusive bandage, are especially effective. One topical composition formed with a vasoline type carrier, such as, AQUAPHOR has been found to be effective.

The inflammatory condition of the joints can be treated by injection at the site of inflammation or by infusion of the drug. Generally, about 200–400 mg of the protease inhibitors can be administered daily by injection or infusion depending on the severity of the disease.

It is understood that the different components used in the treatment of the diseases can be administered in a single unit dose or separately depending upon the patient and the severity of the disease. In most cases, where the patient is a child, the use of a steroid should be avoided.

The corticosteroids which can be used in the treatment of the diseases include triamcinolone acetonide, fluroandrenolide, prednisone, beclomethasone valerate, amcinolone, dexamethasone, betamethasone valerate, halocinonide, clocortolone and hydrocortisone valerate.

The following examples further illustrate the practice of this invention, but are not intended to be limiting thereof. It will be appreciated that the selection of actual amounts of specific protease inhibitor to be administered to any individual patient will fall within the discretion of the attending physician and will be prescribed in a manner commensurate with the appropriate risk: benefit ratio for that particular patient. Appropriate dosages will depend on the patient's age, weight, sex, stage of disease and like factors uniquely within the purview of the attending physician.

EXAMPLE 1

A composition for topical use was prepared as follows:

| Ingredients | Amount |
| --- | --- |
| AQUAPHOR | 200 mg |
| 2% saline solution | 2 ml |
| alpha 1-antitrypsin | 10 mg |
| triamcinolone acetonide | 0.5 mg |

The composition can be applied daily to the site of the skin eruption.

Optional, about 1% by weight of L-arginine and/or hyaluronic acid may be added.

EXAMPLE 2

The drug in liposomes that can be administered orally in order to transgress the gastric barrier and prevent disintegration in the stomach is prepared as follows.

Following the procedure of U.S. Pat. No. 4,239,754, a lipid phase made up of the three components lecithin, cholesterol and dicetyl-phosphate in a molar ratio of 7:2:1 is prepared with 2.6 g of lecithin, 4.4 g of cholesterol and 0.31 g of dicetyl-phosphate by dissolving in 50 ml of chloroform and the solution was evaporated. 0.5 g of alpha 1-antitrypsin was dissolved in saline solution and added to the phospholipids. The mixture is then subject to sonification for 10 seconds.

If desired, a corticosteroid in an amount of 0.01 g can be added to the phospholipid mixture.

What is claimed is:

1. A method for treating an individual suffering from the disease lupus erythematous which comprises administering to the patient a therapeutically effective amount of a composition containing a protease inhibitor selected from the group consisting of alpha 1-antitrypsin, secretory leucocyte protease inhibitor and alpha 2-macroglobulin in a suitable pharmaceutically acceptable carrier, thereby reducing inflammation, rashes or lesions.

2. The method of claim 1 wherein said composition comprises a corticosteroid.

3. The method of claim 1 which comprises topically administering the composition to skin eruptions.

4. The method of claim 1 wherein said composition comprises alpha 1-antitrypsin.

5. The method of claim 4 wherein said composition contains a therapeutic effective amount of hyaluronic acid as a skin penetrating agent.

6. The method of claim 1 wherein said carrier forms an occlusive bandage.

7. The method of claim 1 wherein said composition contains arginine as a skin penetrating agent.

8. The method of claim 7 wherein said composition further contains hyaluronic acid as a skin penetrating agent.

9. The method of claim 1 wherein said composition is administered by infusion.

10. The method of claim 1 wherein said composition is administered by injection.

11. A composition for topically treating the symptoms of systemic lupus erythematous which comprises:

a. about 0.5 to 10% by weight of a protease inhibitor selected from the group consisting of alpha 1-antitrypsin, secretory leucocyte protease inhibitor, and alpha 2-macroglobulin;
b. about 0.5 to 5% by weight of a skin penetrating agent selected from the group consisting of hyaluronic acid, insulin and L-arginine; and
c. a suitable pharmaceutically acceptable carrier.

12. A method of topically treating skin eruptions due to lupus erythematous which comprises administering to the site of eruption an effective amount of a protease inhibitor selected from the group consisting of alpha-1-antitrypsin and secretory leucocyte protease inhibitor in a suitable pharmaceutically acceptable carrier for a time and under conditions effective to reduce scarring.

* * * * *